United States Patent [19]

Corbet et al.

[11] Patent Number: 4,617,290
[45] Date of Patent: Oct. 14, 1986

[54] SYNERGISTINE DERIVATIVES, THEIR PREPARATION AND PHARMACEUTICAL COMPOSITIONS CONTAINING THEM

[75] Inventors: Jean-Pierre Corbet, Ecully; Claude Cotrel, Paris; Daniel Farge, Thiais; Jean-Marc Paris, Vaires sur Marne, all of France

[73] Assignee: Rhone-Poulenc Sante, Courbevoie, France

[21] Appl. No.: 630,245

[22] Filed: Jul. 12, 1984

[30] Foreign Application Priority Data

Jul. 13, 1983 [FR] France ............................ 83 11704

[51] Int. Cl.$^4$ .................. A61K 37/02; C07K 5/12
[52] U.S. Cl. .................................. 514/11; 530/317
[58] Field of Search ............... 260/112.5 R; 514/11

[56] References Cited

PUBLICATIONS

J. Preud'homme, P. Tarridec et A. Belloc, pp. 585–591 (1967).
Chem. Abstr., vol. 99 (1983) 212905.
Chem. Abstr., vol. 76 (1972) 127404.
Chem. Abstr., vol. 63 (1965) 13408.
Merck Index, 9th edition (1976) "Mikamycin and Vinginiamycin", Preud'homme et al., article.
La Presse Medicale, 14–21 Juillet 1984, 13 No. 29, by Mollin.
Chemotherapy 29: 218–224 (1983), by Mutton et al.

Primary Examiner—Delbert R. Phillips
Attorney, Agent, or Firm—Stevens, Davis, Miller & Mosher

[57] ABSTRACT

The invention provides novel synergistine derivatives of the formula:

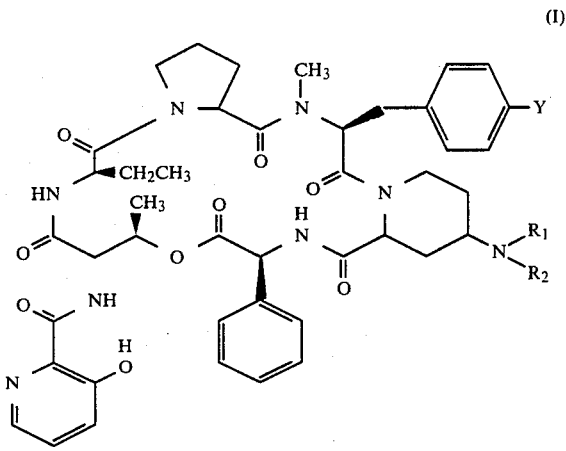

(I)

in which Y=H or N(CH$_3$)$_2$; and R$_1$=H and R$_2$=OH or alkyl optionally substituted by COOH, alkoxycarbonyl or OH or by alkylamino or dialkylamino the alkyl radicals of which can form a heterocycle, or R$_2$=cycloalkyl (of 3 to 7 carbons) or a heterocycle chosen from azetidine, pyrrolidine, piperidine or azepine (optionally substituted on the nitrogen by alkyl), or R$_1$=formyl or alkylcarbonyl and R$_2$=alkyl substituted by COOH or by alkylamino or dialkylamino the alkyl radicals of which can form a heterocycle, or R$_2$ is a heterocycle as defined above, or R$_1$ and R$_2$, which are identical or different, represent alkyl optionally substituted by COOH, alkoxycarbonyl, OH, alkylamino, or dialkylamino of which the alkyl radicals can form a heterocycle, or R$_1$ and R$_2$ form an azetidine, pyrrolidine, piperidine, morpholine or piperazine ring (optionally substituted by alkyl), all the alkyls having 1 to 5 carbon atoms. These compounds are useful as antibacterial agents.

11 Claims, No Drawings

SYNERGISTINE DERIVATIVES, THEIR PREPARATION AND PHARMACEUTICAL COMPOSITIONS CONTAINING THEM

Pristinamycin and virginiamycin are known synergistine compounds: J. Preud'homme et al., Bull., Soc. Chim. Fr. 2, 585–91 (1968).

The present invention provides new synergistine derivatives of the formula:

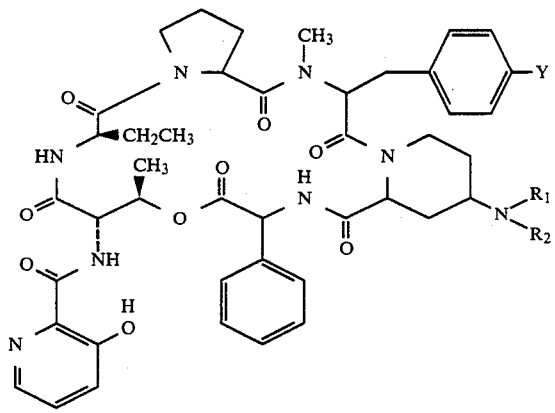
(I)

in which Y is hydrogen or dimethylamino; and $R_1$ is hydrogen and $R_2$ is hydroxyl, alkyl, alkyl substituted (by carboxyl, alkoxycarbonyl, hydroxyl, alkylamino, or dialkylamino, in which the alkyls can form, with the nitrogen atom to which they are attached, a 4-membered to 7-membered heterocycle chosen from azetidinyl, pyrrolidinyl, piperidinyl, piperazinyl, N-alkylpiperazinyl, and azepinyl), or alternatively $R_2$ is cycloalkyl of 3 to 7 carbon atoms or a saturated 4-membered to 7-membered heterocycle chosen from azetidinyl, pyrrolidinyl, piperidinyl and azepinyl, these heterocycles being unsubstituted or substituted on the nitrogen atom by alkyl or $R_1$ is formyl or alkylcarbonyl and $R_2$ is alkyl substituted by carboxyl, alkylamino or dialkylamino in which the alkyls can form, with the nitrogen atom to which they are attached, a 4-membered to 7-membered heterocycle chosen from azetidinyl, pyrrolidinyl, piperidinyl, piperazinyl, N-alkylpiperazinyl and azepinyl, or $R_2$ represents a saturated 4-membered to 7-membered heterocycle chosen from azetidinyl, pyrrolidinyl, piperidinyl and azepinyl, these heterocycles being unsubstituted or substituted on the nitrogen atom by alkyl, or $R_1$ and $R_2$, which are identical or different, are each alkyl or alkyl substituted by carboxyl, alkoxycarbonyl, hydroxyl, alkylamino or dialkylamino in which the alkyls can form, with the nitrogen atom to which they are attached, a 4-membered to 7-membered heterocycle chosen from azetidinyl, pyrrolidinyl, piperidinyl, piperazinyl, N-alkylpiperazinyl and azepinyl, or $R_1$ and $R_2$ together form, with the nitrogen atom to which they are bonded, a 4-membered to 7-membered heterocycle chosen from azetidinyl, pyrrolidinyl, piperidinyl, morpholinyl and piperazinyl unsubstituted or substituted by alkyl; all the aforesaid alkyl radicals and alkyl portions of radicals containing 1 to 5 carbon atoms each in a linear or branched chain; and their pharmaceutically acceptable salts, especially acid addition salts.

According to a feature of the invention, the compounds of the formula (I), with the exception of those in which $R_1$ is formyl or alkylcarbonyl, are prepared by reacting an amine of the formula:

(II)

in which $R_1$ and $R_2$ are as defined above, except that they cannot represent formyl or alkylcarbonyl, with a synergistine of the formula:

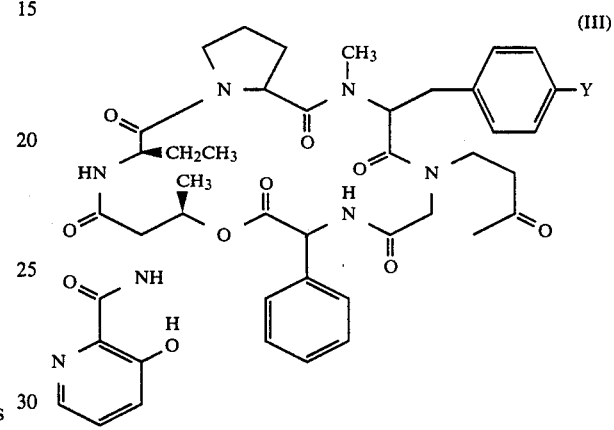
(III)

in which Y is hydrogen (virginiamycin S) or dimethylamino (pristinamycin $I_A$), in the presence of an alkali metal cyanoborohydride.

The reaction is generally carried out with an excess of amine of the general formula (II), in the presence of an alkali metal cyanoborohydride such as sodium cyanoborohydride, in an organic solvent, such as an alcohol, in which hydrogen chloride has been dissolved (methanol containing hydrogen chloride or ethanol containing hydrogen chloride), at a temperature of between 0° C. and the reflux temperature of the reaction mixture, preferably at a temperature of the order of 20° C.

The reaction can advantageously be carried out in the presence of a drying agent such as molecular sieves.

It is understood that if $R_1$ and/or $R_2$ in the general formula (II) represent a radical containing a secondary amine group, this must be protected before reacting the product of the general formula (II) with the product of the general formula (III).

The protection and the freeing of the amine group are carried out by any known method which does not affect the rest of the molecule.

It is particularly advantageous to use the trifluoroacetyl radical as the blocking radical; this can then be removed using an aqueous solution of an alkali metal bicarbonate such as sodium bicarbonate or potassium bicarbonate.

According to the invention, the products of the general formula (I) in which $R_1$ represents a formyl or alkylcarbonyl radical and $R_2$ represents an alkyl radical substituted by a carboxyl radical or by an alkylamino or dialkylamino radical of which the alkyl radicals optionally form, with the nitrogen atom to which they are attached, a 4-membered to 7-membered heterocycle chosen from azetidinyl, pyrrolidinyl, piperidinyl, piperazinyl, N-alkylpiperazinyl or azepinyl, or represents a saturated 4-membered to 7-membered heterocycle chosen from the azetidine, pyrrolidine, piperidine and azepine rings, it being possible for these heterocycles to be substituted on the nitrogen atom by an alkyl radical, and Y is defined as above, can be prepared by reacting a product of the general formula:

R—CO—X (IV)

in which R represents a hydrogen atom or an alkyl radical and X represents a halogen atom or an alkylcarbonyloxy radical, with a product of the general formula:

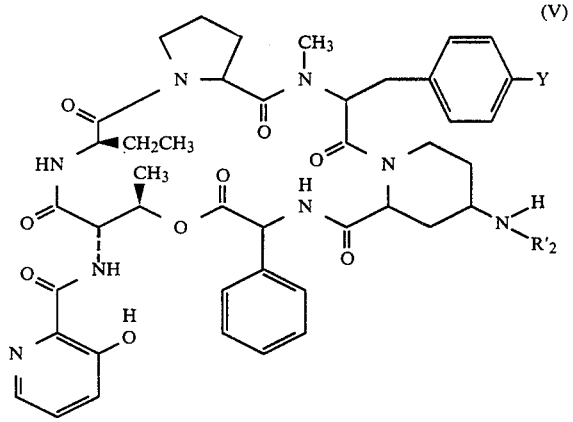

in which Y is defined as above and $R'_2$ has the corresponding definition of $R_2$ given above.

The reaction is generally carried out in an organic solvent such as pyridine, a chlorinated solvent (methylene chloride) or an ether (tetrahydrofuran), in the presence of an acid acceptor such as an organic base like triethylamine, or an inorganic base such as an alkali metal carbonate or bicarbonate like sodium bicarbonate, at a temperature of between 0° C. and 80° C.

Those skilled in the art will understand that if $R'_2$ represents a radical containing a secondary amine group, the said group must be protected before reacting the product of the general formula (IV) with the product of the general formula (V). This can be effected using any customary blocking means employed for protecting an amine group and capable of being removed thereafter, without affecting the rest of the molecule. The reaction is carried out in particular under the conditions described above.

The products of the general formula (I) in which $R_1$ represents a hydrogen atom, $R_2$ represents a hydroxyl radical and Y is defined as above can also be prepared by reducing the products of the general formula:

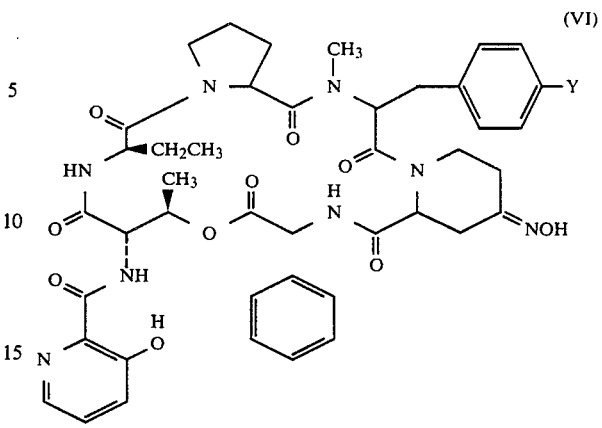

in which Y is defined as above.

The reduction can be carried out by any known method for reducing an oxime to a hydroxylamine without affecting the rest of the molecule. It is particularly advantageous to carry out this reduction by means of an alkali metal cyanoborohydride such as sodium cyanoborohydride, in methanol solution, in the presence of hydrogen chloride.

The amines of the general formula (II) can be obtained by analogy with the method described in J. Amer. Chem. Soc., 54, 1499 (1932) and J. Amer. Chem. Soc., 54, 3441 (1932) (it being understood that if $R_1$ and/or $R_2$ contain an alkylamino radical, this is protected beforehand by any known method which does not affect the rest of the molecule), or alternatively if $R_1$ is a hydrogen atom and $R_2$ is a saturated 4-membered to 7-membered heterocyclyl radical, the amines of the general formula (II) can be prepared by applying the methods described by E. F. Elslager et al., J. Med. Chem., 17, 99 (1974) and L. M. Werbel et al., J. Het. Chem., 10, 363 (1973).

The products of the general formula (VI) can be prepared by reacting hydroxylamine with a product of the general formula (III) according to the known methods.

The new products of the general formula (I) can be purified by the customary known methods such as crystallization, chromatography or successive extractions in an acidic or basic medium. For those skilled in the art who are familiar with the sensitivity of synergistines in an alkaline medium, it is obvious that the term "basic medium" is understood as meaning a medium which is just sufficiently alkaline to free the parent substance from its acid addition salt, i.e. a medium whose pH does not exceed 7.5 to 8.

The new products of the general formula (I) in which the various symbols are defined as above, with the exception of those in the molecule of which $R_1$ represents a formyl or alkylcarbonyl radical and $R_2$ represents an alkyl radical substituted by a carboxyl radical, can be converted to addition salts with acids by reaction with an acid in an organic solvent such as an alcohol, a ketone, an ester or a chlorinated solvent. The salts precipitates, if appropriate after concentration of its solution; it is separated off by filtration or decantation. The acid addition salts can also be obtained in the form of aqueous solutions by the addition of an aqueous solution of the corresponding acid to the product of the general formula (I) such as it has just been defined.

The new products of the general formula (I) in which the radicals $R_1$ and/or $R_2$ represent an alkyl radical substituted by a carboxyl radical can be converted to metal salts or to addition salts with nitrogen bases in a manner analogous to that described above for the acid addition salts, except that the acid is replaced with a metal hydroxide or an organic base.

The synergistines obtained by fermentation are used for the treatment of infections caused by Gram-positive bacteria (of the genera Staphylococcus, Streptococcus, Pneumococcus or Enterococcus) and Gram-negative bacteria (of the genus Haemophilus, Gonococcus or Meningococcus). However, known synergistines have the disadvantage of being insoluble in aqueous media and can therefore only be administered orally, generally in the form of capsules, coated tablets or ordinary tablets. Because of this insolubility, it is impossible to use the known synergistines if the patient is not capable of swallowing; this is the case, in particular, in paediatrics and intensive care, whereas the spectrum of activity of these products would make them a valuable indication in a large number of circumstances, e.g. in cases of comatose septicaemia.

The new compounds of the invention have the considerable advantage of being soluble or capable of being solubilized in water, either in the form of parent substances or in the form of salts, at therapeutically useful levels, while at the same time retaining the general spectrum of antibacterial activity of synergistines. They are especially active in vitro against *Staphylococcus aureus* Smith at concentrations of between 8 and 125 µg/ml.

Their toxicity is generally low. Their $LD_{50}$ is generally greater than 500 mg/kg, when administered subcutaneously to mice.

Of particular value are the compounds of the general formula (I) in which: Y represents hydrogen or dimethylamino and $R_1$ represents hydrogen and $R_2$ represents hydroxyl, alkyl or alkyl substituted by hydroxyl or dialkylamino, or $R_2$ represents piperidinyl unsubstituted or substituted by alkyl, or $R_1$ represents alkylcarbonyl and $R_2$ represents dialkylaminoalkyl, or $R_1$ and $R_2$, which are identical or different, represent alkyl or alkyl substituted by carboxyl or dialkylamino, or together form, with the nitrogen atom to which they are attached, 4-methylpiperazinyl. Among these compounds, those which are more especially active are the compounds of the formula (I) in which: Y represents a dimethylamino radical and $R_1$ represents hydrogen and $R_2$ represents hydroxyl or alkyl of 1 or 2 carbon atoms or alkylpiperidinyl of which the alkyl contains 1 or 2 carbon atoms, or $R_1$ represents alkyl of 1 or 2 carbon atoms and $R_2$ represents alkyl or dimethylamino alkyl, or $R_1$ and $R_2$ together form, with the nitrogen atom to which they are attached, alkylpiperazinyl of which the alkyl contains 1 or 2 carbon atoms, and especially the following products: 5γ-deoxy-5γ-dimethylaminopristinamycin $I_A$, 5γ-deoxy-5γ-methylaminopristinamycin $I_A$, 5γ-deoxy-5γ-[N-(2-dimethylaminoethyl)-N-methylamino]-pristinamycin $I_A$, 5γ-deoxy-5γ-(4-methylpiperazin-1-yl)-pristinamycin $I_A$ and 5γ-deoxy-5γ-hydroxyaminopristinamycin $I_A$.

For use in therapy, the compounds of the invention can be employed as such, i.e. in the form of the base, but for use in aqueous solution, which constitutes the main advantage of the new products it is particularly advantageous to use their pharmaceutically acceptable salts, i.e. salts which are non-toxic at the doses used.

Pharmaceutically acceptable salts which may be mentioned are the addition salts with mineral acids, such as hydrochlorides, hydrobromides, sulphates, nitrates and phosphates, or with organic acids, such as acetates, propionates, succinates, maleates, fumarates, methanesulphonates, p-toluenesulphonates and isethionates, or substitution derivatives of these compounds. Other pharmaceutically acceptable salts which may be mentioned are the salts with alkali metals, such as the sodium, potassium and lithium salts, the salts with alkaline earth metals, such as the magnesium salt, the ammonium salt and the addition salts with organic nitrogen bases such as ethanolamine, diethanolamine, trimethylamine, triethylamine, methylamine, propylamine, diisopropylamine, N,N-dimethylethanolamine, benzylamine, dibenzylamine, dicyclohexylbenzylamine, N-benzyl-β-phenethylamine, N,N'-dibenzylethylenediamine, benzhydrylamine, arginine, leucine, lysine or N-methylglucamine.

The Examples which follow illustrate the invention. The NMR spectra of the products described in these Examples have general characteristics which are common to all the products and particular characteristics which are peculiar to each of the products according to the nature of the substituents Y, $R_1$ and $R_2$. In Example 1, the assignment of all the protons in the molecule is given; in the subsequent Examples, only the particular characteristics due to the variable radicals are mentioned. All the protons are designated according to the numbering indicated in the general formula (VII) and recommended by J. O. ANTEUNIS et al. [Eur. J. Biochim., 58, 259 (1975)].

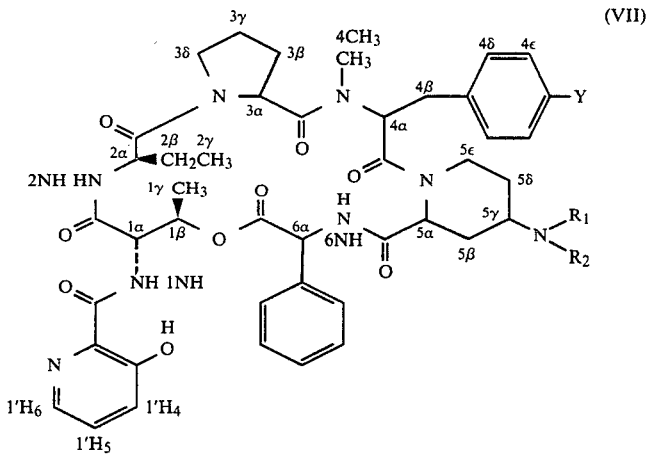

(VII)

All the spectra were run at 250 MHz in deuterchloroform; the chemical shifts are expressed in ppm relative to the signal for tetramethylsilane. The abbreviations used below are as follows:
s = singlet
d = doublet
t = triplet
mt = multiplet
up = unresolved peaks
dd = doublet of doublets
dt = doublets of triplets
ddd = doublet of doublet of doublets
dddd = doublet of doublet of doublet of doublets In Examples 2 to 15, the following are given respectively in brackets: the chemical shift, the shape of the signal, the integration (number of protons, if appropriate with the percentage of isomer) and the assignment of the protons.

In the Examples which follow "flash" chromatography is to be understood as meaning a purification technique which comprises using a short chromatography column and operating under a moderate pressure (50 kPa) using a silica of particle size 40–63 μm, according to the method of W. C. STILL, M. KAHN and A. MITRA [J. Org. Chem., 43, 2923 (1978)].

EXAMPLE 1

Pristinamycin $I_A$ (0.5 g) and sodium cyanoborohydride (20 mg) are added to a solution of 3-dimethylaminopropylamine (0.41 cc) in methanol (15 cc) containing a 2N methanolic solution of hydrogen chloride (2.4 cc), kept at 55° C. The solution obtained is then allowed to return to a temperature of the order of 20° C. for about 2 hours and then concentrated to dryness under reduced pressure (2.7 kPa) at 30° C. The residue obtained is triturated with a mixture of methylene chloride (50 cc) and a saturated aqueous solution of sodium bicarbonate (50 cc); the organic phase is decanted and the aqueous phase is extracted twice with methylene chloride (20 cc in total). The organic phases are combined, dried over magnesium sulphate and filtered and the filtrate is then concentrated to dryness under reduced pressure (2.7 kPa) at 30° C. The residue obtained is purified by "flash" chromatography [eluent: chloroform/methanol (80/20 by volume)]. Fractions 15 to 30 are combined and concentrated to dryness under reduced pressure (2.7 kPa) at 30° C.; the residue obtained is triturated with ethyl ether (5 cc), filtered off and dried under reduced pressure (0.027 kPa) at 20° C. This gives 5γ-deoxy-5γ-(3-dimethylaminopropyl)aminopristinamycin $I_A$ (60 mg) in the form of a cream powder melting at about 160° C.

The complete NMR spectrum has the following characteristics:

| δ(ppm) | Shape of the signal | Assignment |
|---|---|---|
| 8.40 | d | 6 NH |
| 8.25 | d | 1 NH |
| 7.55 | dd | 1'H$_6$ |
| 7.05 | up | 6γ + 6δ + 6ε |
| 7 | dd | 1'H$_4$ |
| 6.90 | dd | 1'H$_5$ |
| 6.70 | d | } 4δ + 4ε |
| 6.40 | d |  |
| 6.50 | d | 2 NH |
| 5.75 | ddd | 1β |
| 5.45 | d | 6α |
| 5.25 | dd | 4α |
| 5 | s (broad) | 5α |
| 4.75 | dd | 1α |
| 4.60 | up | 2α |
| 4.45 | d (broad) | 5ε$_1$ |
| 4.40 | dd | 3α |
| 3.4 | dd (broad) | 3δ$_1$ |
| 3.20 | dd (broad) | 3δ$_2$ |
| 3 | s | 4 CH$_3$ |
| 3 | up | 5γ + 4β$_1$ and 2 |
| 2.80 | s | 4 N(CH$_3$)$_2$ |
| 2.65 | t | —NCH$_2$—(chain) |
| 2.35 | up | 5ε$_2$ + 5β$_1$ |
| 2.25 | t | —NCH$_2$—(chain) |
| 2.20 | s | —N(CH$_3$)$_2$(chain) |
| 1.60 | up | —CH$_2$—(chain) 2β + 3γ |
| 1.25 | d | 1γ |
| 0.90 | t | 2γ |
| 0.50 | dddd | 5β$_2$ |

A 10% aqueous solution of 5γ-deoxy-5γ-(3-dimethylaminopropyl)aminopristinamycin $I_A$ (product A) in the form of the hydrochloride is obtained with:
product A . . . 0.1 g
2N hydrochloric acid . . . 0.52 cc
distilled water . . . q.s. 1 cc

EXAMPLE 2

A 5N ethanolic solution of dimethylamine (2.8 cc) and then a 5N methanolic solution of hydrogen chloride (2 cc) are added to a solution of pristinamycin $I_A$ (2 g) in methanol (25 cc). Sodium cyanoborohydride (76 mg) is added to the resulting solution and the mixture is then stirred for 48 hours at a temperature of the order of 20° C. The reaction mixture is then concentrated to dryness under reduced pressure (2.7 kPa) at 30° C. The residue is triturated with a mixture of methylene chloride (25 cc) and a saturated aqueous solution of sodium bicarbonate (25 cc); the organic phase is decanted and the aqueous phase is extracted twice with methylene chloride (50 cc in total). The organic phases are combined, dried over magnesium sulphate and filtered and the filtrate is then concentrated to dryness under reduced pressure (2.7 kPa) at 30° C. The residue is purified by "flash" chromatography [eluent: chloroform/methanol (92/8 by volume)]. Fractions 5 to 12 are combined and concentrated to dryness under reduced pressure (2.7 kPa) at 30° C. This gives 5γ-deoxy-5γ-dimethylaminopristinamycin $I_A$ (0.7 g) in the form of a beige powder melting at about 170° C.

NMR spectrum: 0.70 (dt, 1H: $5\beta_2$); 2.10 to 2.60 (up, 4H: $5\delta_1+5\delta_2+5\beta_1+5\gamma$); 2.15 (s, 3H×0.8: —N(CH$_3$)$_2$ 1st isomer); 2.20 (s, 3H×0.2: —N(CH$_3$)$_2$ 2nd isomer).

A 2% aqueous solution of 5γ-deoxy-5γ-dimethylaminopristinamycin $I_A$ (product B) in the form of the hydrochloride is obtained with:
product B . . . 0.05 g
0.1N hydrochloric acid . . . 0.56 cc
distilled water . . . q.s. 2.5 cc

EXAMPLE 3

By following a procedure analogous to that described in Example 2, but starting from pristinamycin $I_A$ (1 g), 7N ethanolic solution of methylamine (1 cc) and sodium cyanoborohydride (0.088 g), and after "flash" chromatography [eluent: chloroform/methanol (88/12 by volume)] and concentration to dryness of fractions 11 to 19 under reduced pressure (2.7 kPa) at 30° C., 5γ-deoxy-5γ-methylaminopristinamycin $I_A$ (0.35 g) is obtained in the form of a yellow powder melting at about 185° C.

NMR spectrum: 0.5 (mt, 1H: $5\beta_2$); 2.4 (mt, 6H: —NHCH$_3$+$5\delta_1$+$5\delta_2$+$5\beta_1$); 7.75 (mt, 1H×0.8: 1'H$_6$ 1st isomer); 7.97 (mt, 1H×0.2: 1'H$_6$ 2nd isomer).

A 1% aqueous solution of 5γ-deoxy-5γ-methylaminopristinamycin $I_A$ (product C) in the form of the hydrochloride is obtained with:
product C . . . 0.05 g
0.1N hydrochloric acid . . . 0.57 cc
distilled water . . . q.s. 5 cc

EXAMPLE 4

By following a procedure analogous to that described in Example 2, but starting from pristinamycin $I_A$ (6 g), (2-dimethylaminoethyl)methylamine (5.4 cc), a 5N methanolic solution of hydrogen chloride (18 cc) and sodium cyanoborohydride (0.3 g), and after purification by "flash" chromatography [eluent: chloroform/methanol (85/15 by volume)] and concentration to dryness of fractions 10 to 17 under reduced pressure (2.7 kPa) at 30° C., 5γ-deoxy-5γ-[N-(2-dimethylaminoethyl)-N-methylamino]pristinamycin $I_A$ (1.2 g) is obtained in the form of a white powder melting at about 120° C.

NMR spectrum: 0.75 (dt, 1H: $5\beta_2$); 2.15 (s, 3H: >N—CH$_3$); 2.35 (up, 7H: —N(CH$_3$)$_2$+$5\beta_1$); 2.4 to 2.8 (up, 7H: >N—CH$_2$—CH$_2$—N< +$5\delta_1$+$5\delta_2$+$5\gamma$); 7.75 (mt, 1H: 1'H$_6$ [only 1 isomer]).

A 10% aqueous solution of 5γ-deoxy-5γ-[N-(2-dimethylaminoethyl)-N-methylamino]pristinamycin $I_A$ (product D) in the form of the hydrochloride is obtained with:

product D . . . 0.5 g
1N hydrochloric acid . . . 1.05 cc
distilled water . . . q.s. 5 cc

EXAMPLE 5

By following a procedure analogous to that described in Example 1, but starting from pristinamycin $I_A$ (10 g), 2-dimethylaminoethylamine (6.2 g) and sodium cyanoborohydride (0.38 g), and after purification by "flash" chromatography [eluent: chloroform/methanol (88/12 by volume)] and concentration to dryness of fractions 16 to 30 under reduced pressure (2.7 kPa) at 30° C., 5γ-deoxy-5γ-(2-dimethylaminoethyl)aminopristinamycin $I_A$ (1.1 g) is obtained in the form of a yellow powder melting at about 180° C.

NMR spectrum: 0.8 (up, 1H: $5\beta_2$); 2.3 (s, 6H: —N(CH$_3$)$_2$); 2.4 to 2.8 (up, 8H: >N—CH$_2$CH$_2$—N< +$5\beta_1$+$5\gamma$+$5\delta_1$+$5\delta_2$); 7.70 (mt, 1H×0.75: 1'H$_6$ 1st isomer); 7.95 (mt, 1H×0.25: 1'H$_6$ 2nd isomer).

A 10% solution of 5γ-deoxy-5γ-(2-dimethylaminoethyl)aminopristinamycin $I_A$ (product E) in the form of the hydrochloride is obtained with:
product E . . . 0.1 g
0.2N hydrochloric acid . . . 0.53 cc
distilled water . . . q.s. 1 cc

EXAMPLE 6

A 3 Å molecular sieve (5 g) is added to a solution of pristinamycin $I_A$ (3 g), 4-diethylamino-1-methylbutylamine (3.3 g), sodium cyanoborohydride (0.11 g) and a 5N methanolic solution of hydrogen chloride (9 cc) in methanol (75 cc). The suspension obtained is stirred for 4 days at a temperature of the order of 20° C. and then filtered; the filtrate is concentrated to dryness under reduced pressure (2.7 kPa) at 30° C. The residue is triturated with a mixture of methylene chloride (50 cc) and a saturated aqueous solution of sodium bicarbonate (50 cc); the organic phase is decanted and the aqueous phase is extracted twice with methylene chloride (50 cc in total). The organic phases are combined, dried over magnesium sulphate and filtered and the filtrate is then concentrated to dryness under reduced pressure (2.7 kPa) at 30° C. The residue is purified by "flash" chromatography [eluent: chloroform/methanol (90/10 by volume)]. This gives 5γ-deoxy-5γ-(4-diethylamino-1-methylbutyl)aminopristinamycin $I_A$ (0.7 g) in the form of a beige powder melting at about 160° C.

NMR spectrum: 1.10 (mt, 9H: —N(CH$_2$CH$_3$)$_2$+

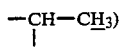

about 1.7 (up, 4H: —CH$_2$—CH$_2$—CH$_2$—N(C$_2$H$_5$)$_2$); 2.90 (up, 6H: —CH$_2$N(CH$_2$CH$_3$)$_2$); 7.70 (mt, 1H×0.45: 1'H$_6$ 1st isomer); 7.77 (mt, 1H×0.55: 1'H$_6$ 2nd isomer).

A 10% aqueous solution of 5γ-deoxy-5γ-(4-diethylamino-1-methylbutyl)aminopristinamycin $I_A$ (product F) in the form of the hydrochloride is obtained with:
product F . . . 0.1 g
0.1N hydrochloric acid . . . q.s. 1 cc

EXAMPLE 7

By following a procedure analogous to that described in Example 1, but starting from pristinamycin $I_A$ (4 g), N-methylpiperazine (2.7 g) and sodium cyanoborohydride (0.16 g), and after purification by "flash" chromatography [eluent: chloroform/methanol (95/5 by volume)] and concentration to dryness of fractions 12 to 23 under reduced pressure (2.7 kPa) at 30° C., 5γ-deoxy-5γ-(4-methylpiperazin-1-yl)pristinamycin $I_A$ (0.7 g) is obtained in the form of a white powder melting at about 195° C.

NMR spectrum: 0.8 (up, 1H: $5\beta_2$); 2.05 to 2.30 (up, 3H: $5\delta_1+5\delta_2+5\gamma$); 2.30 (s, 3H: >N—CH$_3$); 2.50 (up, 9H:

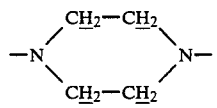

+$5\beta_1$); 7.70 (mt, 1H×0.9: 1'H$_6$ 1st isomer); 7.98 (mt, 1H×0.1: 1'H$_6$ 2nd isomer).

A 10% aqueous solution of 5γ-deoxy-5γ-(4-methylpiperazin-1-yl)pristinamycin $I_A$ (product G) in the form of the hydrochloride is obtained with:
product G . . . 0.1 g
0.2N hydrochloric acid . . . 0.52 cc
distilled water . . . q.s. 1 cc

EXAMPLE 8

By following a procedure analogous to that described in Example 1, but starting from pristinamycin $I_A$ (6.0 g), sodium cyanoborohydride (0.24 g) and 4-amino-1-methylpiperidine (4.65 g), and after purification by "flash" chromatography [eluent: chloroform/methanol (80/20 by volume)] and concentration to dryness of fractions 12 to 36 under reduced pressure (2.7 kPa) at 30° C., 5γ-deoxy-5γ-(1-methylpiperidin-4-ylamino)pristinamycin $I_A$ (1.75 g) is obtained in the form of a beige powder melting at about 195° C.

NMR spectrum: 0.25 (ddd, 1H: $5\beta_2$); 2.3 (up, 3H: >N—CH$_3$); 2.40 (d, 1H: $5\epsilon$); 3 (up, 4H:

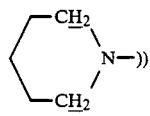

5.10 (s, 1H: $5\alpha$); 7.75 (dd, 1H×0.8: 1'H$_6$ 1st isomer); 8 (dd, 1H×0.2: 1'H$_6$ 2nd isomer).

A 3.7% aqueous solution of 5γ-deoxy-5γ-(1-methylpiperidin-4-ylamino)pristinamycin $I_A$ (product H) in the form of the hydrochloride is obtained with:
product H . . . 0.03 g
0.1N hydrochloric acid . . . 0.8 cc The 4-amino-1-methylpiperidine can be prepared according to the method described by E. F. Elslager et al., J. Med. Chem., 17, 99 (1974).

EXAMPLE 9

By following a procedure analogous to that described in Example 1, but starting from pristinamycin $I_A$ (2 g), hydroxylamine hydrochloride (0.97 g) and sodium cyanoborohydride (0.076 g), and after purification by "flash" chromatography [eluent: chloroform/methanol (95/5 by volume)] and concentration to dryness of fractions 10 to 17 under reduced pressure (2.7 kPa) at 30° C., 5γ-deoxy-5γ-hydroxyaminopristinamycin $I_A$ (1.1 g) is obtained in the form of a white powder melting at about 170° C.

NMR spectrum: 0.4 (up, 1H: $5\beta_2$); 2.45 (d, 1H: $5\beta_2$); 3.1 (d: 5γ in complex unresolved peaks); 7.80 (mt, 1H×0.75: 1'H$_6$ 1st isomer); 7.95 (mt, 1H×0.25: 1'H$_6$ 2nd isomer)

A 10% aqueous solution of 5γ-deoxy-5γ-hydroxyaminopristinamycin $I_A$ (product I) in the form of the hydrochloride is obtained with:
product I . . . 0.1 g
0.2N hydrochloric acid . . . 0.57 cc
distilled water . . . q.s. 1 cc

EXAMPLE 10

Sodium cyanoborohydride (0.7 g) is added to a solution of 5γ-deoxy-5γ-hydroxyiminopristinamycin $I_A$ (12.5 g) in methanol (300 cc) containing a 2N methanolic solution of hydrogen chloride (10 cc). The solution obtained is stirred for 2 days at a temperature of the order of 20° C. and then concentrated to dryness under reduced pressure (2.7 kPa) at 30° C. The residue is triturated in a mixture of methylene chloride (200 cc) and a saturated aqueous solution of sodium bicarbonate (100 cc); the organic phase is decanted and the aqueous phase is extracted with methylene chloride (100 cc). The organic phases are combined, dried over magnesium sulphate and filtered and the filtrate is concentrated to dryness under reduced pressure (2.7 kPa) at 30° C. After purification by "flash" chromatography [eluent: chloroform/methanol (95/5 by volume)], 5γ-deoxy-5γ-hydroxyaminopristinamycin $I_A$ (6.8 g) is obtained in the form of a white powder melting at about 170° C.

The NMR spectrum is identical to that obtained from the product prepared in Example 9.

The 5β-deoxy-5γ-hydroxyiminopristinamycin $I_A$ can be obtained by stirring a solution of pristinamycin $I_A$ (15 g) and hydroxylamine hydrochloride (7.5 g) in methanol (150 cc) containing a 2N methanolic solution of hydrogen chloride (8 cc), for 5 hours, at a temperature of the order of 20° C. The reaction mixture is then concentrated to dryness under reduced pressure (2.7 kPa) at 30° C. The residue is triturated with a mixture of chloroform (100 cc) and a saturated aqueous solution of sodium bicarbonate (100 cc); the organic phase is decanted and the aqueous phase is extracted twice with chloroform (200 cc in total). The organic phases are combined, dried over magnesium sulphate and filtered and the filtrate is concentrated to dryness under reduced pressure (2.7 kPa) at 30° C. This gives 5γ-deoxy-5γ-hydroxyiminopristinamycin $I_A$ (14 g) in the form of a beige powder melting at 210° C.

NMR spectrum: 0.35 (dd, 1H: $5\beta_2$); 3.25 (up, 2H: $4\epsilon_2+5\beta_1$); 5.05 (d, 1H: $5\alpha$); 5.5 (up, 2H including $5\epsilon_1$); 7.80 (dd, 1H×0.40: 1'H$_6$ 1st isomer); 7.90 (dd, 1H×0.60: 1'H$_6$ 2nd isomer).

EXAMPLE 11

By following a procedure analogous to that described in Example 1, but starting from pristinamycin $I_A$ (4 g), 3-aminopropan-1-ol (3 g) and sodium cyanoborohydride (0.16 g), and after purification by "flash" chromatography [eluent: chloroform/methanol (90/10 by volume)] and concentration to dryness of fractions 9 to 16 under reduced pressure (2.7 kPa) at 30° C., 5γ-deoxy-5γ-(3-hydroxypropyl)aminopristinamycin $I_A$ (1.1 g) is obtained in the form of a cream powder melting at about 160° C.

NMR spectrum: 0.45 (up, 1H: $5\beta_2$); 1.70 (up, 2H: —CH$_2$—CH$_2$—CH$_2$—); 2.0 (up, 1H: $5\delta$); 2.40 (up, 2H: $5\delta+5\beta_1$); 2.90 (up, 2H: —NH—CH$_2$—); 3.30 (up: 5γ);

3.75 (t, 2H: —CH₂—OH); 7.80 (mt, 1H×0.9: 1'H₆ 1st isomer); 7.95 (mt, 1H×0.1: 1'H₆ 2nd isomer).

A 2% aqueous solution of 5γ-deoxy-5γ-(3-hydroxypropyl)aminopristinamycin I$_A$ (product J) in the form of the hydrochloride is obtained with:
product J . . . 0.1 g
0.1N hydrochloric acid . . . 1.08 cc
distilled water . . . q.s. 5 cc

EXAMPLE 12

By following a procedure analogous to that described in Example 6, but starting from pristinamycin I$_A$ (4 g), N-methylaminoacetic acid (2.5 g) and sodium cyanoborohydride (0.076 g), and after purification by "flash" chromatography [eluent: chloroform/methanol (80/20 by volume)] and concentration to dryness of fractions 6 to 12 under reduced pressure (2.7 kPa) at 30° C., 5γ-[N-(carboxymethyl)methylamino]-5γ-deoxypristinamycin I$_A$ (0.8 g) is obtained in the form of a cream powder melting at about 140° C.

NMR spectrum: 1.15 (up, 1H: 5β₂); 2.2 (up, 2H: 5δ₁+5δ₂) 2.40 (up, 4H: >N—CH₃+5β₁); 2.8 (up: 5γ); 3.5 (up, 2H: >N—CH₂CO₂H); 8.0 (mt, 1H: 1'H₆).

A 2% aqueous solution of 5γ-[N-(carboxymethyl)methylamino]-5γ-deoxypristinamycin I$_A$ (product K) is obtained with:
product K . . . 0.2 g
distilled water . . . q.s. 10 cc

EXAMPLE 13

Acetyl chloride (0.3 cc) is added to a solution of 5γ-deoxy-5γ-(2-dimethylaminoethyl)aminopristinamycin I$_A$ (3.2 g) in chloroform (50 cc) containing triethylamine (0.6 cc). The reaction mixture is stirred for 30 minutes at a temperature of the order of 20° C. and then concentrated to dryness under reduced pressure (2.7 kPa) at 30° C. The residue is purified by "flash" chromatography [eluent: chloroform/methanol (90/10 by volume)]; by concentration to dryness of fractions 10 to 21 under reduced pressure (2.7 kPa) at 30° C., 5γ-deoxy-5γ-[N-(2-dimethylaminoethyl)-acetamido]pristinamycin I$_A$ (1.8 g) is obtained in the form of a white powder melting at about 170° C.

NMR spectrum: 0.9 (up, 4H: 2γ+5β₂); 2.05 to 2.15 (up, 3H: 5δ₁+5δ₂+5γ); 2.15 (s, 3H: —COCH₃); 2.45 (s, 6H: —N(CH₃)₂); 2.35 to 2.60 (up, 5H: >N—CH₂—CH₂—N< +5β₁); 7.8 (mt, 1H×0.75: 1'H₆ 1st isomer); 8.25 (mt, 1H×0.25: 1'H₆ 2nd isomer).

A 10% aqueous solution of 5γ-deoxy-5γ-[N-(2-dimethylaminoethyl)acetamido]pristinamycin I$_A$ (product L) in the form of the hydrochloride is obtained with:
product L . . . 0.1 g
0.2N hydrochloric acid . . . 0.51 cc
distilled water . . . q.s. 1 cc The 5γ-deoxy-5γ-(2-dimethylaminoethyl)aminopristinamycin I$_A$ can be prepared as described in Example 5.

EXAMPLE 14

By following a procedure analogous to that described in Example 13, but starting from 5γ-deoxy-5γ-(3-dimethylaminopropyl)aminopristinamycin I$_A$ (2.4 g) and acetyl chloride (0.2 cc), and after purification by "flash" chromatography [eluent: chloroform/methanol (90/10 by volume)] and concentration to dryness of fractions 13 to 18 under reduced pressure (2.7 kPa) at 30° C., 5γ-deoxy-5γ-[N-(3-dimethylaminopropyl)acetamido]-pyristinamycin I$_A$ (1.6 g) is obtained in the form of an ochre powder melting at 210° C.

NMR spectrum: 0.8 (up, 1H: 5β₂); 1.4 (up, 2H: —CH₂CH₂—CH₂—); 2.20 (s: —COCH₃ 1st isomer); 2.40 (s: —COCH₃ 2nd isomer); 2.6 (s, 6H: —N(CH₃)₂); 2.4 to 2.6 (up, 1H: 5γ); 2.9 (up, 2H: —CH₂N<); 7.8 (mt, 1H×0.9: 1'H₆ 1st isomer); 8.0 (mt, 1H×0.1: 1'H₆ 2nd isomer).

A 10% aqueous solution of 5γ-deoxy-5γ-[N-(3-dimethylaminopropyl)acetamido]pristinamycin I$_A$ (product M) in the form of the hydrochloride is obtained with:
product M . . . 0.1 g
0.2N hydrochloric acid . . . 0.5 cc
distilled water . . . q.s. 1 cc The 5γ-deoxy-5γ-(3-dimethylaminopropyl)aminopristinamycin I$_A$ can be prepared as described in Example 1.

EXAMPLE 15

By following a procedure analogous to that described in Example 1, but starting from virginiamycin S (2.5 g) and sodium cyanoborohydride (0.1 g), and after purification by "flash" chromatography [eluent: chloroform/methanol (90/10 by volume)] and concentration to dryness of fractions 8 to 15 under reduced pressure (2.7 kPa) at 30° C., 5γ-deoxy-5γ-(3-dimethylaminopropyl)aminovirginiamycin S (0.17 g) is obtained in the form of a beige powder melting at about 140° C.

NMR spectrum: 0.6 (ddd, 1H: 5β₂); 1.65 (up, 2H: —NHCH₂—CH₂—CH₂N<); 2.25 (s, 6H:

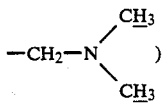

2.35 and 2.70 (up, 4H: —NH—CH₂—CH₂CH₂—N<); 3.20 (d, 1H: 5ε₂); 5.20 (up, 1H: 5α); 7.70 (dd, 1H: 1'H₆).

A 10% aqueous soluton of 5γ-deoxy-5γ-(3-dimethylaminopropyl)aminovirginiamycin S (product N) in the form of the hydrochloride is obtained with:
product N . . . 10 mg
0.2N hydrochloric acid . . . 0.055 cc
distilled water . . . q.s. 0.1 cc The present invention includes within its scope pharmaceutical compositions comprising a compound of formula (I), in the free form or in the form of an addition salt with a pharmaceutically acceptable acid or, if appropriate, a pharmaceutically acceptable base, in association with one or more pharmaceutically acceptable diluents or adjuvants. The compositions may also contain other pharmaceutically compatible product, which may be inert or physiologically active. The drugs according to the invention can be administered parenterally, rectally, orally or topically.

The sterile compositions for parenteral administration can preferably be suspensions, emulsions or aqueous or non-aqueous solutions. Water, propylene glycol, polyethylene glycol, vegetable oils, in particular olive oil, injectable organic esters, e.g. ethyl oleate, or other suitable organic solvents can be employed as the solvent or vehicle. These compositions can also contain adjuvants, in particular wetting agents, agents for imparting isotonicity, emulsifiers, dispersants and stabilizers. Sterilization can be carried out in several ways, e.g. by filtration under aseptic conditions, by incorporating sterilizing agents into the composition, by irradiation or by heating. The compositions can also be prepared in the form of sterile solid compositions which can be dissolved in an injectable sterile medium at the time of use.

The compositions for rectal administration are suppositories or rectal capsules, which contain, in addition to the active principle, excipients such as cocoa butter, semi-synthetic glycerides or polyethylene glycols.

Tablets, pills, powders or granules can be used as solid compositions for oral administration. In these compositions, the active product according to the invention (if appropriate in association with another pharmaceutically compatible product) is mixed with one or more inert diluents or adjuvants such as sucrose, lactose or starch. These compositions can also comprise substances other than diluents, e.g. a lubricant such as magnesium stearate.

Solutions, suspensions, syrups and elixirs containing inert diluents such as water or paraffin oil, and pharmaceutically acceptable emulsions, can be used as liquid compositions for oral administration. These compositions can also comprise substances other than diluents, e.g. wetting, sweetening or flavouring products.

The compositions for topical administration can be e.g. creams, ointments, lotions, eye lotions, mouthwashes, nose drops or aerosols.

The invention includes within its scope a method of killing or inhibiting the growth of bacteria, e.g. those mentioned above, which comprises exposing said bacteria to contact with an effective bactericidal or bacteriostatic concentration of a compound of formula (I) (or salt thereof).

In human therapy, the compounds of the invention are particularly useful in the treatment of infections of bacterial origin. The dose used depends on the desired effect and the duration of the treatment. For an adult, the dose is generally between 2000 and 4000 mg per day, administered parenterally in particular intravenously by slow perfusion, administered normally while symptoms of infection persist. In general, the physician will determine the dosage which he considers to be most appropriate as a function of the age, the weight and all the other factors peculiar to the subject to be treated.

The Examples which follow illustrate compositions according to the invention.

EXAMPLE A

An injectable solution for perfusion is prepared which contains 10 g/liter of active product and has the following composition:
5γ-deoxy-5γ-dimethylaminopristinamycin $I_A$: 10 g
0.1N aqueous solution of hydrochloric acid: 110 cc
distilled water q.s.: 1000 cc.

EXAMPLE B

An injectable solution for perfusion is prepared which contains 5 g/liter of active product and has the following composition:
5γ-deoxy-5γ-methylaminopristinamycin $I_A$: 5 g
0.1N aqueous solution of hydrochloric acid: 57 cc
distilled water q.s.: 1000 cc
We claim:
1. A synergistine of the formula:

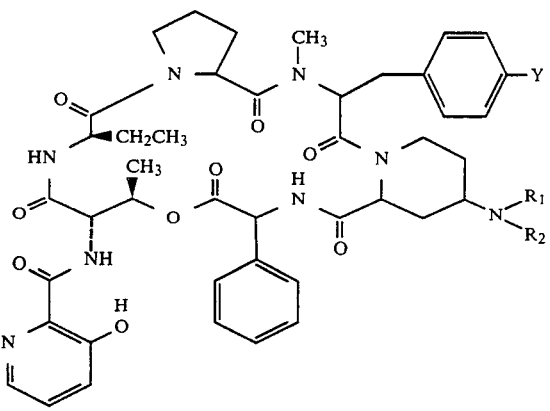

in which Y is hydrogen or dimethylamino; and
(I) $R_1$ is hydrogen and $R_2$ is
 (i) hydroxyl,
 (ii) alkyl,
 (iii) alkyl substituted by carboxyl, alkoxycarbonyl, hydroxyl, alkylamino, dialkylamino, or dialkylamino in which the alkyls form, with the nitrogen atom to which they are attached, a 4-membered to 7-membered heterocycle chosen from azetidinyl, pyrrolidinyl, piperidinyl, piperazinyl, N-alkylpiperazinyl and azepinyl, (iv) cycloalkyl of 3 to 7 carbon atoms, or (v) a saturated 4-membered to 7-membered heterocycle chosen from azetidinyl, pyrrolidinyl, piperidinyl and azepinyl, these heterocycles being unsubstituted or substituted on the nitrogen atom by alkyl; or
(II) $R_1$ is formyl or alkylcarbonyl and $R_2$ is
 (i) alkyl substituted by carboxyl,
 (ii) alkylamino,
 (iii) dialkylamino,
 (iv) dialkylamino in which the alkyls form, with the nitrogen atom to which they are attached, a 4-membered to 7-membered heterocycle chosen from azetidinyl, pyrrolidinyl, piperidinyl, piperazinyl, N-alkylpiperazinyl and azepinyl, or
 (v) a saturated 4-membered to 7-membered heterocycle chosen from azetidinyl, pyrrolidinyl, piperidinyl and azepinyl, these heterocycles being unsubstituted or substituted on the nitrogen atom by alkyl; or
(III) $R_1$ and $R_2$, which are identical or different, are each alkyl which is unsubstituted or substituted by carboxyl, alkoxycarbonyl, hydroxyl, alkylamino, dialkylamino, or dialkylamino in which the alkyls form, with the nitrogen atom to which they are attached, a 4-membered to 7-membered heterocycle chosen from azetidinyl, pyrrolidinyl, piperidinyl, piperazinyl, N-alkylpiperazinyl and azepinyl, or
(IV) $R_1$ and $R_2$ together form, with the nitrogen atom to which they are bonded, a 4-membered to 7-membered heterocycle chosen from azetidinyl, pyrrolidinyl, piperidinyl, morpholinyl, piperazinyl, and piperazinyl substituted by alkyl; all the aforesaid alkyl radicals and alkyl portions of radicals containing 1 to 5 carbon atoms each in a linear or branched chain; and its pharmaceutically acceptable salts.

2. A synergistine according to claim 1 in which Y represents hydrogen or dimethylamino and
  (I) $R_1$ represents hydrogen and $R_2$ represents
    (i) hydroxyl,
    (ii) alkyl,
    (iii) alkyl substituted by hydroxyl or dialkylamino, or
    (iv) piperidinyl unsubstituted or substituted by alkyl,
  or
  (II) $R_1$ represents alkylcarbonyl and $R_2$ represents dialkylaminoalkyl, or
  (III) $R_1$ and $R_2$, which are identical or different, are each alkyl which is unsubstituted or substituted by carboxyl or dialkylamino, or
  (IV) $R_1$ and $R_2$ together form, with the nitrogen atom to which they are attached, 4-methylpiperazinyl, and its pharmaceutically acceptable salts.

3. A synergistine according to claim 1 in which Y represents a dimethylamino and
  (I) $R_1$ represents hydrogen and $R_2$ represents hydroxyl, alkyl of 1 or 2 carbon atoms, or alkylpiperidinyl of which the alkyl contains 1 or 2 carbon atoms, or
  (II) $R_1$ represents alkyl of 1 or 2 carbon atoms and $R_2$ represents alkyl or dimethylaminoalkyl, or
  (III) $R_1$ and $R_2$ together form, with the nitrogen atom to which they are attached, alkylpiperazinyl in which the alkyl contains 1 or 2 carbon atoms, and its pharmaceutically acceptable salts.

4. A synergistine according to claim 1 which is 5γ-deoxy-5γ-dimethylaminopristinamycin $I_A$ and its pharmaceutically acceptable salts.

5. A synergistine according to claim 1 which is 5γ-deoxy-5γ-methylaminopristinamycin $I_A$ and its pharmaceutically acceptable salts.

6. A synergistine according to claim 1 which is 5γ-deoxy-5γ-[N-(2-dimethylaminoethyl)-N-methylamino]-pristinamycin $I_A$ and its pharmaceutically acceptable salts.

7. A synergistine according to claim 1 which is 5γ-deoxy-5γ-(4-methyl-piperazin-1-yl)-pristinamycin $I_A$ and its pharmaceutically acceptable salts.

8. A synergistine according to claim 1 which is 5γ-deoxy-5γ-hydroxyaminopristinamycin $I_A$ and its pharmaceutically acceptable salts.

9. A pharmaceutical composition useful as an antibacterial agent which contains an effective antibacterial amount of a synergistine according to claim 1, or a pharmaceutically acceptable salt thereof in association with one or more pharmaceutically compatible diluents or adjuvants.

10. A pharmaceutical composition according to claim 9 in the form of a sterile injectable solution of a pharmaceutically acceptable salt of a said synergistine.

11. A method of killing or inhibiting the growth of bacteria in a host in which antibacterial therapy is required which comprises exposing said bacteria to contact with an effective amount of a synergistine as claimed in claim 1 or a pharmaceutically acceptable salt thereof.

* * * * *